US006479051B1

(12) United States Patent
Bruce et al.

(10) Patent No.: US 6,479,051 B1
(45) Date of Patent: Nov. 12, 2002

(54) ORAL ADMINISTRATION OF LACTOBACILLUS FOR THE TREATMENT AND PREVENTION OF UROGENITAL INFECTION

(75) Inventors: Andrew W. Bruce, Toronto; Gregor Reid, London, both of (CA)

(73) Assignee: Urex Biotex, Inc., London (CA)

( * ) Notice: Subject to any disclaimer, the term of this patent is extended or adjusted under 35 U.S.C. 154(b) by 0 days.

(21) Appl. No.: 09/459,292

(22) Filed: Dec. 10, 1999

Related U.S. Application Data

(60) Provisional application No. 60/111,965, filed on Dec. 11, 1998.

(51) Int. Cl.[7] .................................................. C12N 1/20
(52) U.S. Cl. .................................................. 424/93.45
(58) Field of Search ........................ 514/8; 424/93.45, 424/234.1, 430, 535, 282.1; 435/252.9, 244, 853–857

(56) References Cited

U.S. PATENT DOCUMENTS

| | | | | |
|---|---|---|---|---|
| 5,733,568 A | * | 3/1998 | Ford | 424/433 |
| 6,004,551 A | * | 12/1999 | Reid et al. | 424/93.45 |
| 6,180,100 B1 | * | 1/2000 | Bruce et al. | 424/93.45 |
| 6,051,552 A | * | 4/2000 | Reid et al. | 514/8 |

FOREIGN PATENT DOCUMENTS

| | | |
|---|---|---|
| WO | WO 93/01823 | 2/1993 |
| WO | WO 98/23727 | 6/1998 |

OTHER PUBLICATIONS

Reid, et al. 1990, Clinical Microbiology Reviews, pp. 335–344.*
Rasic J., et al. (1983) "Bifidobacteria and Their Role", *Birkauser Verlag*, pp. 86–101.
Rasic J., et al. (1978) "Yoghurt", *Technical Diary Publishing House*, pp. 120–137.
Reig G., et al. (1998), "Effect of Nutrient Compositions on the In Vitro Growth of Urogential Lactobacilli an Uropathogens", *Can. J. Microbiol.*, 44:866–871.
Sanders M.E. (2000), "Considerations for use of Probiotic Bacteria to Modulate Human Health", *Journal of Nutrition*, 130:384S–390S.
Sieber R., et al. (1998) "Lactobacillus Acidophilus and Yoghurt in the Prevention and Therapy of Bacterial Vaginosis", *International Dairy Journal*, 8:599–607.
International Search Report, PCT/CA99/01182.

* cited by examiner

*Primary Examiner*—Deborah Crouch
*Assistant Examiner*—Joseph Woitach
(74) *Attorney, Agent, or Firm*—Scully, Scott, Murphy & Presser

(57) ABSTRACT

The present invention provides methods and compositions for the oral administration of Lactobacillus and/or other probiotic organisms, such as Bifidobacterium, for establishment and maintenance of a healthy urogenital flora. The invention also provides methods and compositions to reduce the risk of disease.

17 Claims, 5 Drawing Sheets

ORAL ADMINISTRATION OF LACTOBACILLUS FOR THE TREATMENT AND PREVENTION OF UROGENITAL INFECTION

CROSS REFERENCE TO RELATED APPLICATION

This application claims priority from U.S. Provisional Application No. 60/111,965 filed Dec. 11, 1998.

FIELD OF THE INVENTION

The present invention provides methods and compositions for the oral administration of lactobacilli or other probiotic organisms such as Bifidobacterium, for reduction of the risk of urogenital infection and concomitant restoration and/or maintenance of the desired urogenital flora.

BACKGROUND OF THE INVENTION

Urogenital infections, including urinary tract infections (UTI), bacterial vaginosis (BV) and yeast vaginitis, afflict an estimated one billion women in the world annually. While antimicrobial agents are effective at providing clinical remediation, the incidence of infections by multi-drug resistant Gram positive cocci appears to be rising and there is great concern that methicillin resistant *Staphylococcus aureus* (MRSA) and vancomycin resistant enterococci (VRE) may thwart even the most potent antimicrobial agents.

The mode of action of urogenital pathogens is now better understood and involves formation of biofilms in the intestine. Intestinal biofilms then become a reservoir for urogenital pathogens which invade the urogenital tract, where more biofilms are formed. Urogenital tract biofilms then become the reservoir for infection of the vagina (for example by yeast and bacteria causing vaginosis) and the urinary tract (for example by organisms causing urinary tract infections).

Previous studies have shown that specially selected probiotic lactobacilli, provided in a pessary inserted into the vagina, can colonize (Reid, et al. 1994) and compete against colonization of enterococci and other uropathogens (Bruce & Reid, 1998). The art also describes the use of Lactobacillus to prevent and treat urinary and urogenital infections.

SUMMARY OF THE INVENTION

The present invention demonstrates specially selected lactobacilli with antagonistic properties against urogenital pathogens, can colonize the vagina and provide protection against infection after oral intake. The present invention, for the first time, establishes that oral intake of Lactobacillus can successfully deliver probiotic therapy to women in need thereof.

The present invention provides methods and compositions for the treatment and inhibition of urogenital infection caused by pathogenic organisms. Oral administration of Lactobacillus, other probiotic compounds in a pharmaceutically acceptable carrier, such as milk or portions thereof, including yogurt, provide a safe and effective means for colonizing the intestine, urinary tract and vagina and treating, inhibiting or reducing the occurrence of urogenital infections.

In the practice of the compositions and methods of the present invention, the Lactobacillus may be administered as viable whole cells. The Lactobacillus species may be aerobically grown or microaerophillically grown and selected from *L. rhamnosus, L. acidophilus, L. crispatus, L. fermentum, L. plantarum, L. casei, L. paracasei, L. jensenil, L. gasseri, L. cellobiosis, L. brevis, L. delbrueckii, L. rogosae* and *L. bifidum*.

The present invention provides a method for preventing, treating or reducing the occurrence of urogenital infections in a mammal in need of such treatment by oral administration of Lactobacillus.

In one embodiment of the present invention a method is provided for establishing a healthy gastrointestinal and urogenital flora in females throughout life comprising orally administering a therapeutically effective amount of at least one probiotic organism and a pharmaceutically acceptable carrier. In a further embodiment of the method a therapeutically effective amount of a second probiotic organism is administered. Lactobacillus is the preferred probiotic organism. Bifidobacteria is the preferred second probiotic organism. The Bifidobacterium is preferably selected from the group consisting of *B. bifidum, B. breve, B. adolescentis,* or *B. longum*.

In another embodiment, the present invention describes a method for improving the intestinal, urogenital and vaginal microenvironment by oral administration of Lactobacillus.

In still another embodiment, the present invention provides a method for inhibiting, treating or reducing the occurrence of urogenital infections in a mammal in need of such treatment by oral administration of Lactobacillus and other probiotic organisms. In a preferred embodiment, the probiotic organism is Bifidobacterium.

In still yet another embodiment, the present invention describes a method for inhibiting urogenital pathogen colonization of the gastrointestinal and urogenital tract in mammals. In a preferred embodiment, the mammals are humans. In another embodiment, the urogenital pathogens are *Escherichia coli,* Klebsiella spp., Pseudomonas spp., Proteus spp., Providencia spp., Staphylococcus spp. , Streptococcus spp., Bacteroides spp., Mobiluncus spp. Trichomonas spp. Fusobacterium spp., Enterococcus spp., Gardnerella spp. and/or yeast.

In a further embodiment, the present invention describes a method for maintaining healthy urogenital flora by oral intake of Lactobacillus.

In a most preferred embodiment, the Lactobacillus species are *L. rhamnosus* GR-1 (ATCC 55826), *L. fermentum* RC-14 (ATCC 55845) and *L. fermentum* B-54 (ATCC 55884).

In another embodiment, the present invention provides a method for preventing or reducing the biofilm load of urogenital pathogens in the intestine, vagina, perineum and bladder in a mammal in need of such treatment by oral administration of Lactobacillus, anti-urogenital pathogen probiotics together with a suitable carrier.

In still another embodiment, the present invention provides a probe for the detection of lactobacilli in a biological sample.

In a preferred embodiment, the suitable carrier is milk or portions thereof, including yogurt and other such foods, including, but not limited to, milk shakes and powdered milk products; non-milk products and non-lactose containing products, including calcium carbonate.

DETAILED DESCRIPTION OF THE INVENTION

Figure 1:
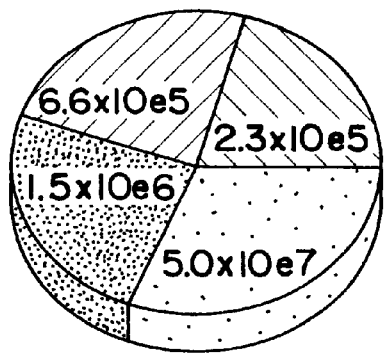
FIG. 1 is a pie chart demonstrating the survival and colonization of *L. rhamnosus GR*-1, *L. fermentum* RC-14 and *L. fermentum* B-54 following oral ingestion in the intestinal tract, as measured in a Day 7 stool sample, from a patient with recurrent urogenital infections. This demonstrates safe passage of probiotic Lactobacillus through the stomach and intestine.

The present invention is directed to methods and compositions for maintaining the health of the urogenital tract, and for treating, inhibiting or reducing the occurrence of urogenital infections in mammals by oral administration of one or more Lactobacillus strains alone or in combination with other probiotic organisms together with a pharmaceutically acceptable carrier. As defined by the present invention, a "probiotic" compound is a mono or mixed culture of microorganisms which when ingested by a mammal, for example a human, affect the host beneficially. A preferred probiotic compound is Bifidobacterium.

Lactobacilli which can be orally administered using the method described in the present invention may be administered as viable whole cells. The Lactobacillus may be aerobically or microaerophillically grown and selected from L. rhamnosus, L. acidophilus, L. crispatus, L. fermentum, L. plantarum, L. casei, L. paracasei, L. jensenii, L. gasseri, L. cellobiosis, L. brevis, L. delbrueckii, L. rogosae and L. bifidum. In a preferred embodiment, the Lactobacillus species are L. rhamnosus GR-1 (ATCC 55826), L. fermentum RC-14 (ATCC 55845) and L. fermentum B-54 (ATCC 55884).

In accordance with the present invention, orally administered Lactobacillus species can colonize the human intestinal, genital and urinary tracts thereby competitively inhibiting and otherwise disrupting or interfering with colonization of urogenital pathogens into biofilms. The orally administered Lactobacillus species can also stimulate the indigenous normal flora of the urogenital tract thereby preventing, treating and/or reducing the occurrence of infections caused by urogenital pathogens. The urogenital pathogens inhibited and otherwise depleted by the Lactobacillus of the present invention include, but are not limited to, Escherichia coli, Klebsiella spp., Pseudomonas spp., Proteus spp., Providencia spp., Staphylococcus spp., Streptococcus spp., Bacteroides spp., Mobiluncus spp. Trichomonas spp. Fusobacterium spp., Enterococcus spp., Gardnerella spp. and yeast.

In accordance with the present invention, following diminuation of the pathogenic biofilms in the intestinal, genital and urinary tracts, the orally administered Lactobacillus of the present invention can maintain healthy urogenital flora. By "healthy urogenital flora" is meant a total lactobacilli count greater than. 10,000 more colony forming units of Lactobacillus than Gram negative rods, yeast and Gram positive cocci. By "diminuation of pathogenic biofilms" is meant flora dominated by lactobacilli with no adherent pathogenic microorganisms (e.g. Enterococcus faecalis) on bladder uroepithelial cells, as measured by conventional urinalysis, or depleted numbers of pathogenic microorganisms (to less than 10 per cell) on vaginal cells.

Also defined within the present invention are compositions suitable for establishing, maintaining or restoring a healthy gastrointestinal and urogenital flora in females throughout life which comprise one or more Lactobacillus viable whole cells, non-viable whole cells or cell wall fragments and a pharmaceutically acceptable carrier. By "throughout life" is meant in the neonatal period, during childhood and in the pre-menopausal and post-menopausal periods. By "healthy gastrointestinal and urogenital flora" is meant flora that is predominantly colonized by non-pathogenic organisms and where there are no signs or symptoms of infection or disease.

In a preferred aspect, the Lactobacillus is aerobically, microaerophilically or anaerobically grown and may be selected from the group consisting of Lactobacillus casei, L. acidophilus, L. plantarum, L. fermentum, L. brevis, L. jensenii, L. crispatus, L. rhamnosus, L. reuteri, L. paracasei, L. gasseri, L. cellobiosis, L. delbrueckii, L. helveticus, L. salivarius, L. collinoides, L. buchneri, L. rogosae and L. bifidium.

The Lactobacillus may be microaerophilically or anaerobically grown and selected from the group consisting of Lactobacillus rhamnosus (GR-1 (ATCC 55826), L. rhamnosus GR-2 (ATCC 55915), L. rhamnosus GR-3 (ATCC 55917), L. rhamnosus GR-4 (ATCC 55916), L. rhamnosus RC-9, L. rhamnosus RC-17 (ATCC 55825), L. casei var alactosus RC-21, L. casei NRC 430, L. casei ATCC 7469, L. rhamnosus 81, L. rhamnosus 76, L. rhamnosus 36W, L. rhamnosus 36g, L. casei RC-65, L. casei RC-15, L. casei 558, L. casei, RC-21, L. casei 55, L. casei 8, L. casei 43, L. plantarum RC-12 (ATCC 5,5895), L. acidophilus RC-25, L. plantarum RC-19, L. jensenii RC-11 (ATCC 55901), L. acidophilus ATCC 4357, L. acidophilus 2099 B, L. acidophilus 2155C, L. acidophilus T-13, L. acidophilus 1807B, L. acidophilus RC-16, L. acidophilus RC-26, L. acidophilus RC-10, L. acidophilus RC-24, L. acidophilus RC-13, L. acidophilus RC-14, L. acidophilus RC-12, L. acidophilus RC-22, L. acidophilus 2099B, L. acidophilus 2155C, L. acidophilus T-13, L. plantarum ATCC 8014, L. plantarum UH 2153, L. plantarum 260, L. plantarum RC-20, L. plantarum 75, L. plantarum RC-6, L. fermentum A-60, L. fermentum B-54 (ATCC 55920), L. cellobiosis RC-2, L. crispatus 1350B and L. crispatus 2142B.

In a further embodiment, the present invention describes a method of administering probiotic organisms orally for restoring a healthy urogenital and intestinal flora over the various life cycle stages of women including pregnancy and post-menopause, wherein the pathogenic flora is dominated by Mobiluncus, Gardnerella, Bacteroides, Fusobacterium, Prevotella, Peptostreptococcus, Porphyrornonas, Mycoplasma or group B streptococci, or *Escherichia coli,* Enterococcus sp, Klebsiella sp, Pseudomnonas sp, Streptococcus sp, Proteus sp, and other pathogens which cause urinary tract infections, and yeast including Candida albicans, for example.

The Lactobacillus useful in accordance with the practice of the present invention preferably attaches to human epithelial cells to a level of about 10 to 165 organisms per cell by hydrophobic, hydrophilic or other adhesion interactions.

In another embodiment, the present invention provides a method for selecting lactobacilli and bifidobacteria useful for improving urogenital health. Criteria are provided herein for characterizing a selected Lactobacillus or Bifidobacterium as candidates for the contemplated methods and compositions of the present invention. The probiotic organisms will exhibit some or all of the following criteria: an ability to: adhere to vaginal and uroepithelial cells by electrostatic, hydrophobic or specific adhesions including but not limited to a collagen binding protein; pass through the stomach and reach the small and large intestine and urogenital tract; grow and persist in the gastrointestinal and urogenital tracts; inhibit the adhesion of urogenital pathogens including organisms which cause urinary tract infection, bacterial vaginosis and/or yeast vaginitis; coaggregate to form a balanced flora; produce acid and other substances such as hydrogen peroxide and/or bacteriocins and bacteriocin-like compounds which inhibit pathogen growth; produce biosurfactant or related by-products of growth which interfere with adhesion of pathogens to cells and materials; resist antimicrobial agents, such as nonoxynol-9 spermicide; and/or enhance the host's immune function to further maintain a healthy urogenital flora. The orally administered lactobacilli of the present invention may be detected in a biological sample from one to about twenty-one days after intake with a molecular probe. In a preferred embodiment the biological sample is stool.

Although this invention is not intended to be limited to any particular mode of application, oral administration of the compositions are preferred. One probiotic organism may be administered alone or in conjunction with a second, different probiotic organism. By "in conjunction with" is meant together, substantially simultaneously or sequentially. The compositions may be administered in the form of tablet, pill or capsule, for example. One preferred form of application involves the preparation of a freeze-dried capsule comprising the composition of the present invention. Another preferred form of application involves the preparation of a lyophilized capsule of the present invention. Still another preferred form of application involves the preparation of a heat dried capsule of the present invention. It has been found that a capsule comprising about $10^9$ probiotic organisms is suitable. In accordance with the present invention a capsule may contain one single or two or more different species of probiotic organism(s).

By "amount effective" as used herein is meant an amount of probiotic organism, e.g., Lactobacillus, high enough to significantly positively modify the condition to be treated but low enough to avoid serious side effects (at a reasonable benefit/risk ratio), within the scope of sound medical judgment. An effective amount of Lactobacillus will vary with the particular goal to be achieved, the age and physical condition of the patient being treated, the severity of the underlying disease, the duration of treatment, the nature of concurrent therapy and the specific Lactobacillus employed. The effective amount of Lactobacillus will thus be the minimum amount which will provide the desired attachment to epithelial cells. The presence of $1\times10^9$ bacteria, as viable or non-viable whole cells, in 0.05 ml solution of phosphate buffered saline solution, or in 0.05 ml of suspension of agar, or the dry weight equivalent of cell wall fragments, is effective when administered in quantities of from about 0.05 ml to about 20 ml.

A decided practical advantage is that the probiotic organism, e.g. Lactobacillus, may be administered in a convenient manner such as by the oral, intravenous (where non-viable), or suppository (vaginal or rectal) routes. Depending on the route of administration, the active ingredients which comprise probiotic organisms may be required to be coated in a material to protect said organisms from the action of enzymes, acids and other natural conditions which may inactivate said organisms. In order to administer probiotic organisms by other than parenteral administration, they should be coated by, or administered with, a material to prevent inactivation. For example, probiotic organisms may be co-administered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport lactobacilli or their by-products to the urogenital surface.

The probiotic organisms may also be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the probiotic organisms in the required amount in the appropriate solvent with various of the other ingredients enumerated above, as required, followed by filtered sterilization. Generally, dispersions are prepared by incorporating the various sterilized probiotic organisms into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof. Additional preferred methods of preparation include but are not limited to lyophilization and heat-drying.

When the probiotic organisms are suitably protected as described above, the active compound may be orally administered, for example, with an inert diluent or with an assimilable edible carrier, or it may be enclosed in hard or soft shell gelatin capsule, or it may be compressed into tablets designed to pass through the stomach (i.e., enteric coated), or it may be incorporated directly with the food of the diet. For oral therapeutic administration, the probiotic organisms may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains about $1 \times 10^9$ viable or non-viable e.g., lactobacilli per ml.

The tablets, troches, pills, capsules, and the like, as described above, may also contain the following: a binder such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, lactose or saccharin may be added or a flavoring agent such as peppermint, oil or wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules or lactobacilli in suspension may be coated with shellac, sugar or both.

A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the probiotic organism may be incorporated into sustained-release preparations and formulations.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of the probiotic organisms calculated to produce the desired therapeutic effect in association with the required pharmaceutical carrier. The specification for the novel dosage unit forms of the invention are dictated by and directly depending on (a) the unique characteristics of the probiotic organism and the particular therapeutic effect to be achieved, and (b) the limitations inherent in the art of compounding such probiotic for the establishment and maintenance of a healthy urogenital flora.

The probiotic organism is compounded for convenient and effective administration in effective amounts with a suitable pharmaceutically or food acceptable carrier in dosage unit form as hereinbefore disclosed. A unit dosage form can, for example, contain the principal active compound in an amount approximating $10^9$ viable or non-viable, e.g., lactobacilli, per ml. In the case of compositions containing supplementary ingredients such as prebiotics, the dosages are determined by reference to the usual dose and manner of administration of the said ingredients.

The pharmaceutically acceptable carrier may be in the form of milk or portions thereof including yogurt. Skim milk, skim milk powder, non-milk or non-lactose containing products may also be employed. The skim milk powder is conventionally suspended in phosphate buffered saline (PBS), autoclaved or filtered to eradicate proteinaceous and living contaminants, then freeze dried heat dried, vacuum dried, or lyophilized.

Some other examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry. extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tabletting agents, stabilizers, anti-oxidants and preservatives, can also be present.

Accordingly, in a preferred form of establishing, maintaining or restoring a healthy gastrointestinal and urogenital flora, the patient is orally administered a therapeutically effective amount of at least one probiotic organism and a pharmaceutically acceptable carrier in accordance with the present invention. A most preferred probiotic organism is a Lactobacillus. Preferably, the Lactobacillus is selected from the group comprising *L. rhamnosus, L. casei ss alactosus, L. fermentum* and *L. brevis*. Most preferably, the lactobacillus is either *L. rhamnosus* GR-1, *L, fermentum* B-54 or *L. acidophilus* RC-14.

In order to further illustrate the present invention, the experiments described in the following examples were carried out. It should be understood that the invention is not limited to the specific examples or the details described therein. The results obtained from the experiments described in the examples are shown in the accompanying figures.

EXAMPLE 1

Orally ingested lactobacilli traversed the gastrointestinal tract and reached and colonized the vagina.

Each morning and last thing at night for 14 days, ten women swallowed a probiotic solution containing $>10^9$ *L. rhamnosus* GR-1 and *L. fermentum* RC-14 suspended in 3 ml sterilized skim milk (stored at −20° C.). These organisms were selected on the basis of their production of various antagonistic factors against urogenital pathogens (Reid (1999) *Appl. Environ. Microbiol.*, 65: 3763–3766, incorporated herein by reference), including biosurfactants which inhibit adhesion of Gram positive cocci including enterococci, staphylococci and Group B streptococci, and Gram negative rods including coliforms and Gardnerella. The patients provided urine and vaginal swabs pre-treatment and 1, 2,.3 and 4 weeks after commencement of the therapy. Strains GR-1 and RC-14 were identified by colony and Gram stain morphology and molecular typing (Zhang, et al. (1998) *Appl. Environ. Microbiol.*, 64:2418–2423). During therapy, patients refrained from ingestion of any other probiotic or probiotic compound.

The patients were followed for up to 3 months. Vaginal swabs taken prior to therapy confirmed patients were free from current infection but had depleted lactobacilli numbers. After therapy, strains GR-1 and RC-14 were recovered from the vagina on the first three weeks following oral ingestion, as confirmed by culture and morphology as well as genomic fingerprinting using PCR amplified ribosomal RNA spacers.

The results showed that GR-1 and/or RC-14 were recovered from the vagina within one week in all 10 patients (Table 1). Patient AL did not provide samples after week one and patient SH received antibiotic therapy for bronchitis after week 3. In three of the patients who provided vaginal samples at week 8 and 12, strains GR-1 and RC-14 were recovered. No side effects were noted.

All patients reported improved well being with therapy. This included relief of symptoms of urogenital infection, and no need for monthly yeast therapy. In the caseof JA, the enterococci (present as 1,000 per ml urine prior to therapy) were eradicated from her bladder and vagina (from 200,000 to 0 per ml) within seven days (Example 3). At one year follow-up and continuing daily intake of GR-1 and RC-14, patient JA has remained infection-free. A probe which was specific for strain RC-14 was developed based upon the 16S-23S RNA gene intergenic spacer region. The probe further verified and confirmed the presence of the strain RC-14 in stool and vaginal specimens. (See Example 2).

analysis using specific primers of L. fermentum RC14. The following method was employed:

Lactobacilli isolates were cultured at 37° C. for 48 hours on an LBS plate in anaerobic chamber. One loop of bacteria colonies was picked from the LBS plate and suspended in 1 ml of $d_2H_2O$, then centrifuged for 1 min at 12,000 rpm. 200 µl of InstaGene matrix (Bio-Rad) was added to the pellet and incubated at 56° C. in a water bath for 30 min. The pellet was vortexed at high speed for 10 seconds keeping the sample in the boiling waterbath for 8 min. The sample was-vortexed at high speed again and spun at 12,000 rpm for 3 min. The chromosomal DNA was stored at −20° C. until used.

Optimal PCR conditions for different strains of Lactobacillus were established by using two universal primers from E. coli. The DNA fragment containing the spacer regions between 16S rRNA and 23S rRNA genes of RC-14 strains was amplified by using PCR with two universal primers A1

TABLE 1

Presence of lactobacilli and identification of GR-1 and RC-14: Week of Swab Collection Post Start of Therapy on Day 1

| Patient | 1 yr. history | Preswab | Week 1 | Week 2 | Week 3 | Week 4 | Week 8 | Week 12 |
|---------|---------------|---------|--------|--------|--------|--------|--------|---------|
| CK | RYV | No. Lacto. | ++ GR-1 | ++ GR-1 | ++ GR-1 | ++ GR-1, RC-14 | ++ GR-1 | ++ GR-1 |
| TR | RYV, UTI | Low Lacto. | + GR-1 | ++ GR-1 | NS | ++ RC-14 | ++ GR-1 | ++ GR-1, RC-14 |
| SH | RYV | No Lacto. | + GR-1 | +++ GR-1, RC-14 | ++ RC-14 | ++ Ant RC-14 | | |
| BC | RBV | Low. Lacto. | + RC-14 | ++ GR-1 | ++ RC-14 | + | | |
| AD | RYV | Lacto. | + GR-1 | + GR-1 | + GR-1 | ++ GR-1 | | |
| AC | RYV | Lacto. | + RC-14 | + | NS | ++ RC-14 | | |
| SB | RBV, RYV | Lacto. | + RC-14 | + RC-14 | + RC-14 | | | |
| SO | RYV | Lacto. | ++ GR-1 | ++ GR-1 | ++ GR-1, RC-14 | ++ GR-1, RC-14 | | |
| JA | UTI, RYV | Lacto. | ++[a] | ++[a] | ++[a] | ++[a] | ++[a] | ++[a] |
| AL | UTI, RYV | Lacto | + RC-14 | NS | NS | NS | | |

Legend:
RYV = recurrent yeast vaginitis;
RBV = recurrent bacterial vaginosis;
UTI = recurrent urinary tract infections in past year;
No Lacto = MRS agar plate culture isolated no lactobacilli;
Low Lacto = less than 1- colonies at zero dilution;
+, ++, +++ = 1, 2, or 3 Lactobacillus isolated by colony morphology and Gram stain;
GR-1, RC-14 = identification of GR-1 or RC-14 by colony and Gram stain morphology; and/or molecular typing;
Ant = patient prescribed antibiotics for bronchitis.
NS = no sample collected.
[a] = GR-1 and RC-14 are both recovered at each sampling time.

This data provides conclusive proof that two probiotic lactobacilli, specifically selected for their ability to inhibit urogenital pathogen growth and adhesion, colonized the vagina following oral intake. Notably, in each patient, one or both of the strains colonized the vagina, and remained several months thereafter.

EXAMPLE 2

Lactobacilli were rapidly detected in stool and vaginal specimens via intergenic 16S-23S Ribosomal spacer PCR and B1 from E. coli. The 5' primer, 5'AGTCGTAACAAG-GTAAGCCG3' (SEQ ID NO:1) corresponds to a conserved sequence motif from the 3' end of 16S rRNAs [Primer A1, position 1493–1513 (Escherichia Coli 16S rRNA numbering)] and the 3' primer, 5'C T/C A/G T/C TGC-CAAGCATCCACT3' (SEQ ID NO:2) was deduced from an alignment of the 13 23S 5' sequences [primer B1, position 23–43 (Escherichia coli 23S rRNA numbering)], respectively. DNA templates (1.6 ug, 40 µl) were amplified in a 100 µl reaction volume that contained 2.5 u Taq polymerase (Boehringer Mannheim), 100 ng of each of the primers, 4 mM MgCl$_2$, 0.2 mM of each of the four dNTPs (Pharmacia Biotech), 10 mM Tris-Cl (PH 8.0), 50 mM KCl and 1% (v/v) Triton X-100. Reaction mixtures were overlaid with 100 μl mini oil (liquired paraffin, VWR) and preheated at 95° for 5 min. Amplification was carried out in a AMPLITRON II Thermolyne for 40 cycles. Each amplification cycle was as follows: 30 seconds at 95° C. (denaturation) , 1 min. at 40° C., 45° C. or 50° C. The optimal annealing temperature was 40° C. for RC-14, and 1 min at 72° C. (extension). Post dwell 7 min. at 72° C. Controls were included in each set of amplifications. The controls consisted of a reaction mixture with no DNA template added.

Analysis of the degree and the specificity of PCR products was conducted by 2.5% agarose gel in 1× TAE buffer, running at 70 Volts for 2½ hours. The gel was stained with ethidium bromide and photographed under UV light. DNA fragment sizes were compared with the 100 bp DNA Molecular Weight (Gibco-Life Tech.) There were two PCR bands for RC14 (Band 1: 220 bp and Band 2: 180 bp).

A QIAquick Gel Extraction Kit (Qiagen, Mississauga, Ontario) for extraction of DNA fragments 70 bp-10 kb from standard agrose gel in TAE or TBE buffer was used to purify PCR bands.

Each of the two PCR DNA fragment bands were excised from the agarose gel with a scalpel and the gel slice was weighed. The protocol of QIAquick Gel Extraction Kit was then followed. The Kit system combined the spin-column with the silica-gel membrane. The DNA band was dissolved completely with solubilization buffer in 50° C. for 10 min. DNA adsorbed to the silica membrane in the high salt conditions. Pure DNA was eluted with Tris buffer (PH 8.0). This pure PCR product was stored at −20° C. for later use.

Each PCR band product was ligated into pGEM-T vector (Promega). Each PGEM-T vector was transformed into *E. coli* JM 109 high efficiency competent cells by using Transformation Aid (MBI Fermentas Inc.) on the LB plate with 50 ug/ml ampicillin. Several white colonies or light blue colonies were selected as positive colonies which contained the PCR insert. Colonies were cultured on the LB-ampicillin plate. Each plate contained 32 different colonies. Colonies were cultured with LB-ampicillin broth. One part of culture was frozen quickly by using liquid nitrogen and was kept at −80° C. Another part of culture was used for further miniprep of plasmid DNA. The remainder of culture was kept at 4° C.

The QIAprep Spin Miniprep Kit (Qiagen, Mississauga, Ontario) was used to prepare plasmid DNA. Each of two PCR products was automatically sequenced by using T7 & SP6 promoter primers with two directions. Analysis of sequence was performed using the sequence analysis software package—DNA Star program.

DNA templates (1.6 ug, 40 μl) were amplified in a 100 μl reaction volume that contained 2.5 u Taq polymerase (Boehringer Mannheim), 100 ng of each of the primer, 4 mM MgCl$_2$, 0.2 mM of each of the four dNTPs (Pharmacia Biotech), 10 mM Tris-C1 (PH 8.0), 50 mM KCl, and 1% (v/v) Triton X-100. Reaction mixtures were overlaid with 100 μl mini oil and preheated at 95° C. for 5 min. Amplification was carried out in a AMPLITRON II Thermolyne for 25 cycles. Each amplification cycle was as follows: 30 seconds at 95° C. (denaturation), 1 min. at 60° C. (annealing), and 1 min. at 72° C. (extension). Post dwell 7 min. at 72° C. Controls were included in each set of amplifications. *L. acidophilus* RC-14 was identified in both stool and vaginal specimens (see Example 1 and FIG. 7).

Verification and confirmation of detection of *Lactobacillus fermentum* RC-14 was performed using a traditional API 50 commercial biochemistry test (API Systems, La. Balme, Les Grottes, France) and PCR primer. Organisms were isolated from stool following 10 days of oral intake of the probiotic organism in skim milk suspension (TABLE 3).

TABLE 3

| Patient | Day of isolation | API50 | Molecular Probe |
|---------|------------------|-------|-----------------|
| TO | 7 | RC-14 | RC-14 |
| TO | 14 | RC-14 | RC-14 |
| DR | 7 | RC-14 | RC-14 |
| FH | 7 | RC-14 | RC-14 |

EXAMPLE 3

This example illustrates the extent to which biofilm formation, undetected by most conventional diagnostic systems, can occur in the vagina and thereby seed and infect the bladder. Furthermore, the example illustrates how oral ingestion of lactobacilli, selected for their proven ability to interfere with the adhesion and growth of pathogens, can allow the host to restore a normal urogenital biofilm, thereby reducing the signs and symptoms of infection and restoring a healthy flora, comprising the patient's own lactobacilli as well as those ingested.

A 48 year old woman presented with a four year history of chronic symptomatic UTI which caused constant and often severe suprapubic pain, frequency, urgency and dysuria. Conventional laboratory culture of her urine was repeatedly reported as negative, and several specialist clinics had proposed treatments as varied as removal of the uterus, removal of the sigmoid colon and urethral stretching, all of which were refused by the patient. Careful urinalysis by the inventor showed 1,000 colony forming units of *Enterococcus faecalis*, and examination of the sloughed transitional bladder cells of the patient showed heavy colonization with a mean of 28 enterococci per each of 50 cells.

The patient orally received one vial of probiotic containing >10$^9$ *L. rhamnosus* GR-1 and *L. fermentum* RC-14 suspended in 3 ml sterilized skim milk (stored at −20° C.) each morning and another last thing at night for 14 days. The patient provided urine and vaginal swabs on Days 6, 15 and 21, 28 and 39 for culture and identification of lactobacilli, uropathogens and yeast. Strains GR-1 and RC-14 were identified by morphology on agar plate and under Gram stain microscopy, as well as molecular typing by genomic fingerprinting of GR-1 and RC-14 using PCR amplified ribosomal RNA spacers (i.e., a molecular probe) (see Example 2). Versalovic, et al. (1991) *Nucl. Acids Res.* 19:6823–31 and Versalovic, et al. (1993) *J. Infect. Dis.* 167:850–856 plus Zheng,; et al. (1998) *Appl. Environ. Microbiol.* 64:2418–2423, incorporated herein by reference.

It was determined that two probiotic strains survived stomach acid and bile, and migrated to the vaginal mucosa where they colonized. In addition, the enterococci, which were seeding the bladder from their heavy biofilm presence in the urogenital tract, became depleted after only six days probiotic therapy and were subsequently eradicated from the bladder and significantly reduced in the vagina within two to three weeks. The oral probiotic treatment alleviated the patient's symptoms, eradicated the urinary tract infection and restored a healthy urogenital flora within three weeks.

These experiments show, for the first time, that probiotic lactobacilli can be delivered to the vagina, colonize and restore a healthy flora by oral intake.

EXAMPLE 4

Strains of Lactobacillus species found in the vagina of healthy women, namely, *L. rhamnosus, L. acidophilus, L. crispatus, L. fermentum, L. plantarum, L. casei, L. paracasel, L. jensenii, L. gasseri, L. cellobiosus, L. brevis, L. delbrueckii, L. rogosae, L. bifidum,* with properties such as those possessed by GR-1, RC-14 and B-54 or other defined strains with properties identified previously (Reid & Bruce, 1998) can colonize the vagina following oral ingestion. Evidence of this was found in a 37 year old woman whose stool and vagina contained the same strain of *L. paracasei* spp. *paracasei.* This result further verifies that the intestinal tract is the source of Lactobacillus in the urogenital tract and therefore oral ingestion can lead to Lactobacillus strains colonizing the intestinal and urogenital tracts, as demonstrated in FIGS. 1 and 2 and Examples 1 and 3.

EXAMPLE 5

Figure 2:
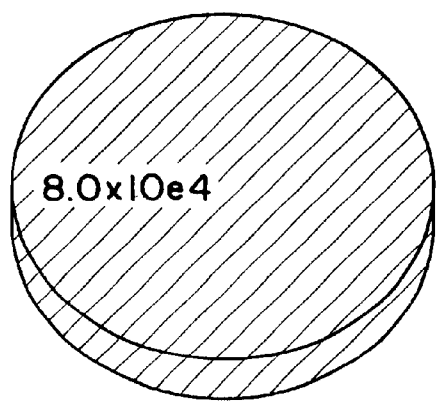
FIG. 2 is a pie chart demonstrating the survival and colonization by L. fermentum RC-14 following oral ingestion in the intestinal tract, as measured in a Day 14 stool sample, from a patient with recurrent urogenital infections. This also demonstrates safe passage through the stomach and intestine and ability of lactobacillus to ascend into the urogenital tract.
Figure 3:
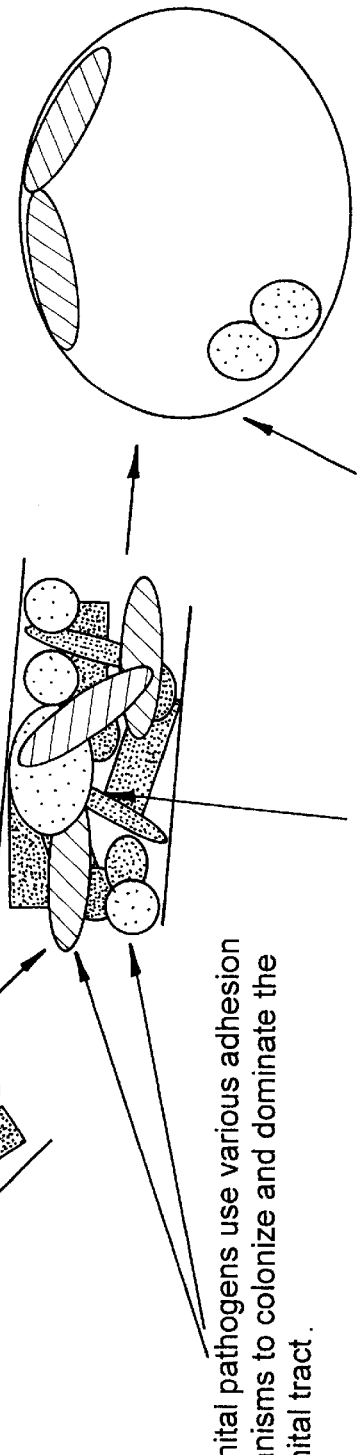
FIG. 3. is a schematic depicting the process of urinary tract and vaginal infection.
Figure 4:
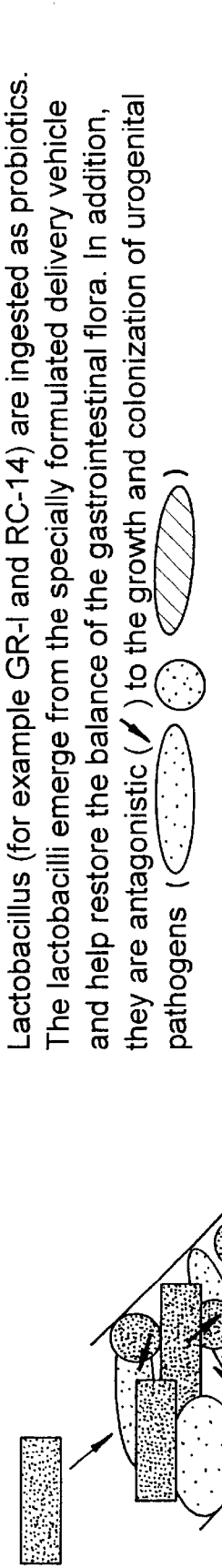
FIG. 4 is a schematic depicting the effect of lactobacillus ingestion on urogenital pathogens in the intestine and vagina.
Figure 4:
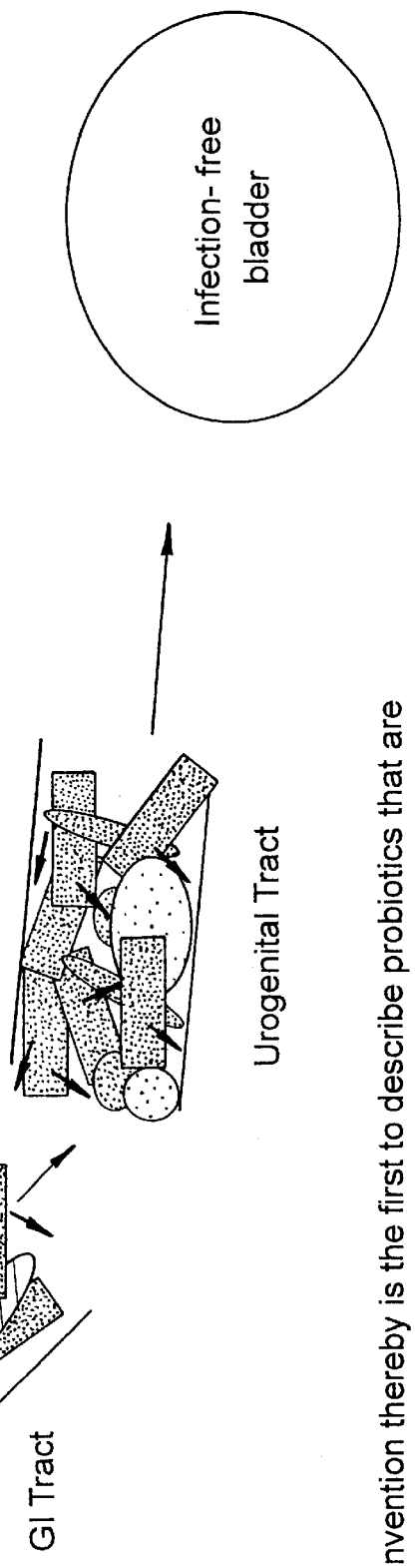
Figure 5:
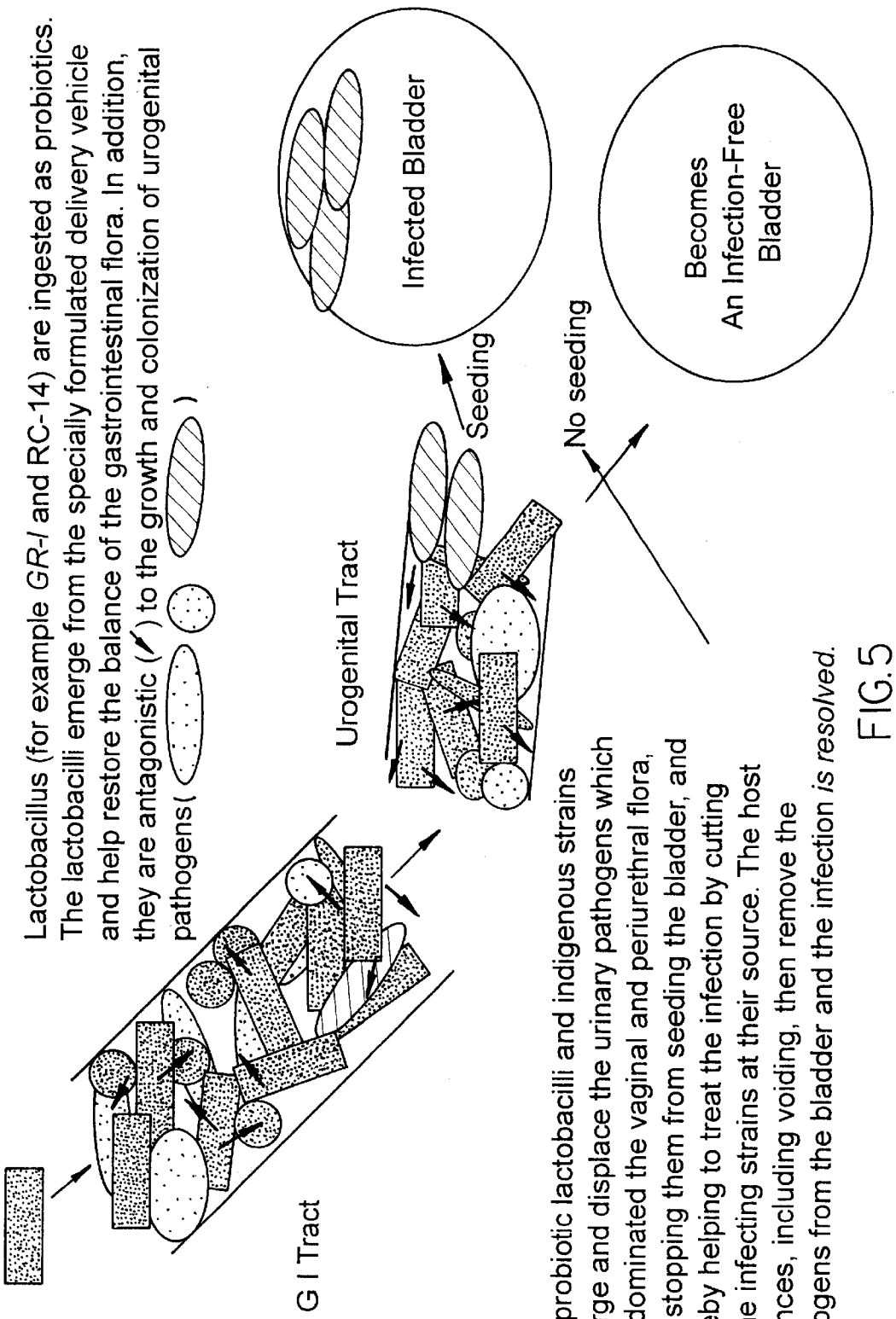
FIG. 5 is a schematic depicting the effect of lactobacillus treatment for urinary tract infection.
Figure 6:
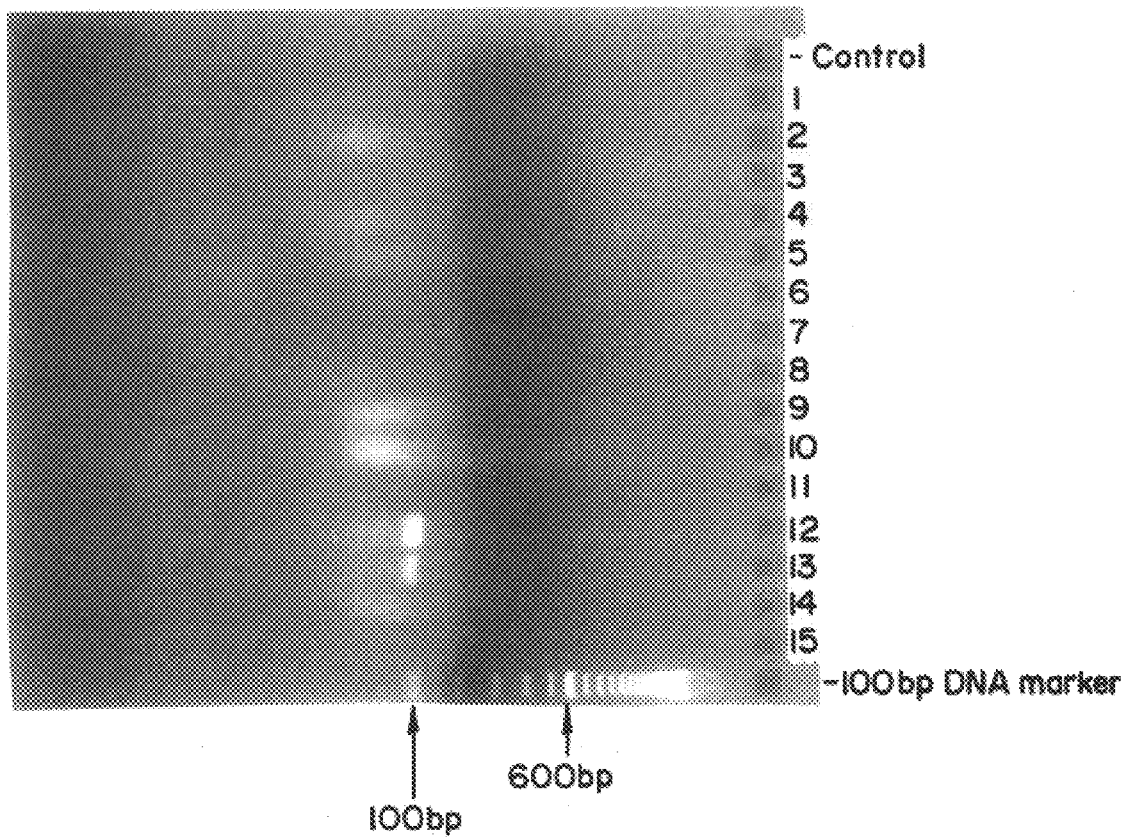
FIG. 6 is a polyacrylamide gel electrophoresis showing PCR products identified. Lane 1—L. rham. ATCC 7469; Lane 2—L. rham. GR-1; Lane 3—L. rham C3-A; Lane 4—L. casei ssp. casei ATCC 393; Lane 5—L. Para. ssp. para. ATCC 25302; Lane 6—L. plant. ATCC 14917; Lane 7—L. ferm. ATCC 14931; Lane 8—L. ferm. ATCC 23271; Lane 9—L. ferm. ATCC 8289; Lane 10—L. ferm. ATCC 11739; Lane 11—L. ferm. ATCC 14932; Lane 12—L. ferm. RC14 (1 band); Lane 13—(L. ferm. B54 has the same ribotype as RC14) (1 band); Lane 14—L. acid. ATCC 4356; Lane 15—L. jensenii ATCC 25258.

Strains *L. rhamnosus* GR-1, *L. fermentum* RC-14 *L. fermentum* B-54 and Bifidobacterium were ingested orally for ten days by three female volunteers. All strains survived the stomach and bile and colonized the intestine, thereby reducing the risk of urogenital infection by uropathogens (FIGS. 1 and 2).

2. The method of claim 1 further comprising the administration of a therapeutically effective amount of at least one second probiotic organism.

3. The method of claim 2 wherein said second probiotic organism is a Bifidobacterium.

4. The method of claim 2 wherein said second probiotic organism is selected from the group consisting of *B. bifidum, B. breve, B. adolescentis,* or *B. longum.*

5. A method of maintaining a healthy urogenital flora in females prior to, during and after pregnancy comprising orally administering at least one probiotic organism selected from the group consisting of *Lactobacillus rhamnosus* GR-1 (ATCC 55826), *L. rhamnosus* GR-2 (ATCC 55915), *L. rhamnosus* GR-3 (ATCC 55917), *L. rhamnosus* GR-4 (ATCC 55916), *L. rhamnosus* RC-17 (ATCC 55825), *L. rhamnosus* RC-12 (ATCC 55895), *L. jensenii* RC-11 (ATCC 55920), *L. acidophilus* ATCC 4357, *L. acidophilus* RC-14 (ATCC 55845), *L. plantarum* RC-20 (ATCC 55883), *L. plantarum* RC-6 (ATCC 55894), *L. fermentum* A-60 (ATCC 55896), *L. fermentum* B-54 (ATCC 55884), and a pharmaceutically acceptable carrier.

6. The method of claim 5 further comprising administration of a therapeutically effective amount of at least one second probiotic organism.

7. The method of claim 6 wherein said second probiotic organism is a Bifidobacterium.

What is claimed is:

1. A method of establishing a healthy urogenital flora in females throughout life comprising orally administering a therapeutically effective amount of at least one probiotic organism selected from the group consisting of *Lactobacillus rhamnosus* GR-1 (ATCC 55826), *L. rhamnosus* GR-2 (ATCC 55915), *L. rhamnosus* GR-3 (ATCC 55917), *L. rhamnosus* GR-4 (ATCC 55916), *L. rhamnosus* RC-17 (ATCC 55825), *L. rhamnosus* RC-12 (ATCC 55895), *L. jensenii* RC-11 (ATCC 55920), *L. acidophilus* ATCC 4357, *L. acidophilus* RC-14 (ATCC 55845), *L. plantarum* RC-20 (ATCC 55883), *L. plantarum* RC-6 (ATCC 55894), *L. fermentum* A-60 (ATCC 55896), *L. fermentum* B-54 (ATCC 55884), and a pharmaceutically acceptable carrier.

8. A method of treating and preventing urogenital infections in women comprising orally administering at least one Lactobacillus selected from the group consisting of *Lactobacillus rhamnosus* GR-1 (ATCC 55826), *L. rhamnosus* GR-2 (ATCC 55915), *L. rhamnosus* GR-3 (ATCC 55917), *L. rhamnosus* GR-4 (ATCC 55916), *L. rhamnosus* RC-17 (ATCC 55825), *L. rhamnosus* RC-12 (ATCC 55895), *L. jensenii* RC-11 (ATCC 55920), *L. acidophilus* ATCC 4357, *L. acidophilus* RC-14 (ATCC 55845), *L. plantarum* RC-20 (ATCC 55883), *L. plantarum* RC-6 (ATCC 55894), *L. fermentum* A-60 (ATCC 55896), *L. fermentum* B-54 (ATCC 55884), and a pharmaceutically acceptable carrier.

9. The method according to claim 8, further comprising orally administering probiotic organisms.

10. The method according to claim 9, wherein said probiotic organism is Bifidobacterium.

11. A method of improving and restoring the urogmnital microenvironment comprising orally administering at least one Lactobacillus selected from the group consisting of *Lactobacillus rhamnosus* GR-1 (ATCC 55826), *L. rhamnosus* GR-2 (ATCC 55915), *L. rhamnosus* GR-3 (ATCC 55917), *L. rhamnosus* GR-4 (ATCC 55916), *L. rhamnosus* RC-17 (ATCC 55825), *L. rhamnosus* RC-12 (ATCC 55895), *L. jensenii* RC-11 (ATCC 55920), *L. acidophilus* ATCC 4357, *L. acidophilus* RC-14 (ATCC 55845), *L. plantarum* RC-20 (ATCC 55883), *L. plantarum* RC-6 (ATCC 55894), *L. fermentum* A-60 (ATCC 55896), *L. fermentum*.

12. A method of inhibiting urogenital pathogen colonization of the urogenital tract in humans comprising oral administration of at least one *Lactobacillus rhamnosus* GR-1 (ATCC 55826), *L. rhamnosus* GR-2 (ATCC 55915), *L. rhamnosus* GR-3 (ATCC 55917), *L. rhamnosus* GR-4 (ATCC 55916), *L. rhamnosus* RC-17 (ATCC 55825), *L. rhamnosus* RC-12 (ATCC 55895), *L. jensenii* RC-11 (ATCC 55920), *L. acidophilus* ATCC 4357, *L. acidophilus* RC-14 (ATCC 55845), *L. plantarum* RC-20 (ATCC 55883), *L. plantarum* RC-6 (ATCC 55894), *L. fermentum* A-60 (ATCC 55896), *L. fermentum* B-54 (ATCC 55884), and a pharmueutically acceptable carrier.

13. A method of reducing the biofilm load of urogenital pathogens comprising orally administering at least one Lactobacillus selected from the group consisting of *Lactobacillus rhamnosus* GR-1 (ATCC 55826), *L. rhamnosus* GR-2 (ATCC 55915), *L. rhamnosus* GR-3 (ATCC 55917), *L. rhamnosus* GR-4 (ATCC 55916), *L. rhamnosus* RC-17 (ATCC 55825), *L. rhamnosus* RC-12 (ATCC 55895), *L. jensenii* (ATCC 55920), *L. acidophilus* ATCC 4357, *L. acidophilus* RC-14 (ATCC 55845), *L. plantarum* RC-20 (ATCC 55883), *L. plantarum* RC-6 (ATCC 55894), *L. fermentum* A-60 (ATCC 55896), *L. fermentum* B-54 (ATCC 55884), in an amount effective to colonize the intestine and the vagina.

14. The method of claim 13, wherein said urogenital pathogens are selected from the group consisting of Klebsiella spp., Pseudomonas spp., Proteus spp., Providencia spp., Staphylococcus spp., Streptococcus spp., Bacteroides spp., Mobiluncus spp. Trichomonas spp. Fusobacterium spp., *Escherichia coli*, Enterococcus spp., Gardnerella spp. or yeast.

15. The method of any one of claim 8, 11, 12 or 13 wherein said pharmaceutically acceptable carrier is milk or portions thereof.

16. The method of claim 15, wherein said milk portions comprise yogurt.

17. A method of delivering a probiotic organism to the vagina comprising orally administering at least one Lactobacillus selected from the group consisting of *Lactobacillus rhamnosus* GR-1 (ATCC 55826), *L. rhamnosus* GR-2 (ATCC 55915), *L. rhamnosus* GR-3 (ATCC 55917), *L. rhamnosus* GR-4 (ATCC 55916), *L. rhamnosus* RC-17 (ATCC 55825), *L. rhamnosus* RC-12 (ATCC 55895), *L. jensenii* RC-11 (ATCC 55920), *L. acidophilus* ATCC 4357, *L. acidophilus* RC-14 (ATCC 55845), *L. plantarum* RC-20 (ATCC 55883), *L. plantarum* RC-6 (ATCC 55894), *L. fermentum* A-60 (ATCC 55896), *L. fermentum* B-54 (ATCC 55884), and a pharmaceutically acceptable carrier.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer A1,
      position 1493-1513, E. Coli 16S

<400> SEQUENCE: 1
agtcgtaaca aggtaagccg                                              20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Primer B1,
      position 23-43, E.Coli 23S

<400> SEQUENCE: 2
cyrytgccaa gcatccact                                               19